United States Patent [19]

Marshall et al.

[11] 4,075,248
[45] Feb. 21, 1978

[54] PRODUCTION OF SYRINGEALDEHYDE FROM HARDWOOD WASTE PULPING LIQUORS

[75] Inventors: Harry Borden Marshall, Senneville; Donald L. Vincent, Pointe Claire, both of Canada

[73] Assignee: Domtar Limited, Montreal, Canada

[21] Appl. No.: 720,628

[22] Filed: Sept. 7, 1976

[51] Int. Cl.² ............................................. C07C 45/00
[52] U.S. Cl. ............................ 260/600 R; 260/600 A
[58] Field of Search ........................ 260/600 A, 600 R

[56] References Cited

U.S. PATENT DOCUMENTS

| 2,506,540 | 5/1950 | Bryan | 260/600 A |
| 2,576,752 | 11/1951 | Fisher et al. | 260/600 A |
| 2,692,291 | 10/1954 | Bryan | 260/600 A |

OTHER PUBLICATIONS

A.T.S. translation of: Kamaldina, Khim. Navka i Pron., vol. 2, No. 4, (1957), pp. 462–465.

Primary Examiner—Bernard Helfin
Attorney, Agent, or Firm—C. A. Rowley

[57] ABSTRACT

Syringealdehyde and vanillin are produced from alkaline or neutral sulphite waste liquors by alkaline oxidative treatment of the liquor and subsequent isolation of a mixture of the aldehydes. Syringealdehyde is separated from vanillin by fractional distillation.

6 Claims, 1 Drawing Figure

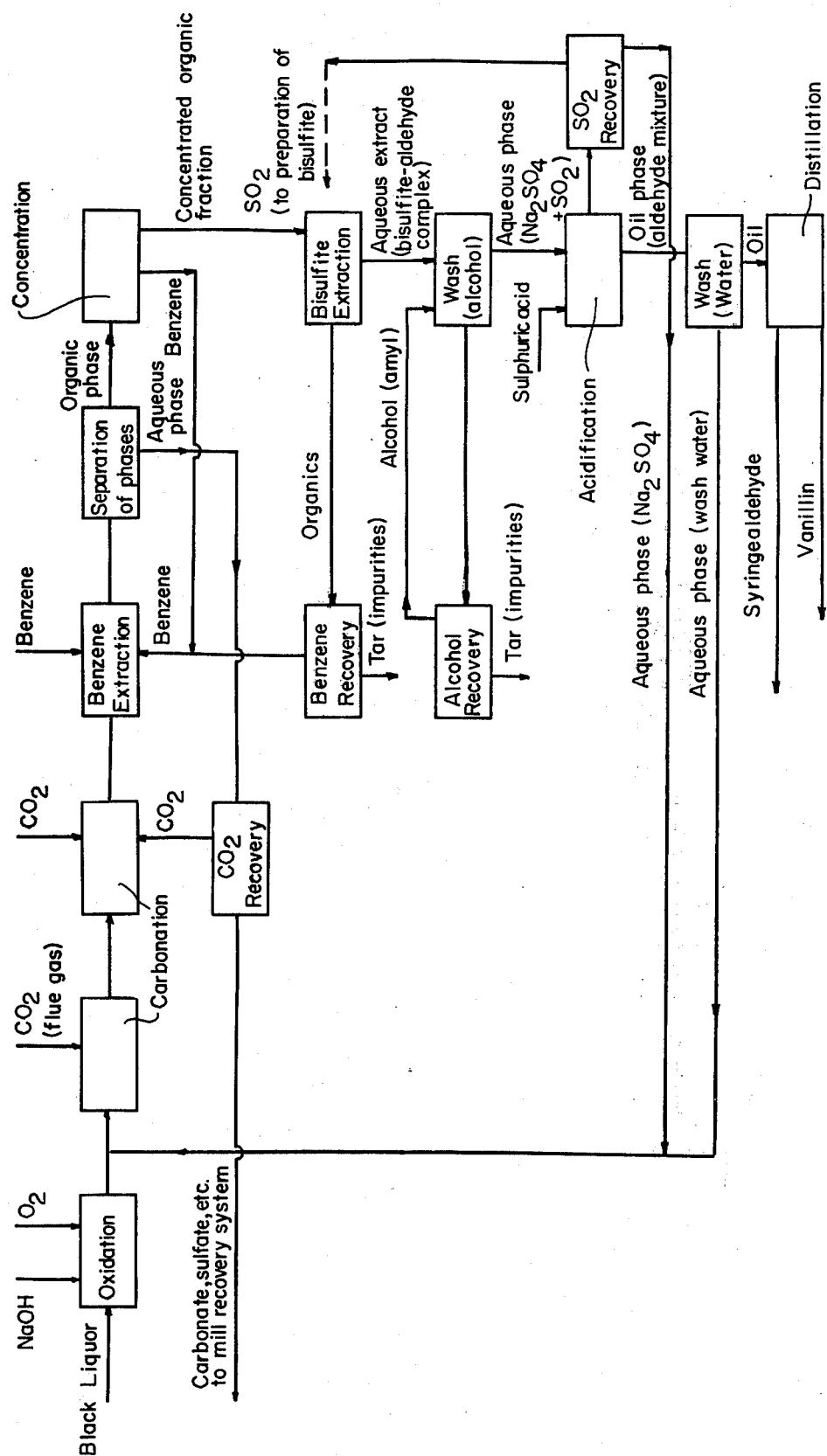

PRODUCTION OF SYRINGEALDEHYDE FROM HARDWOOD WASTE PULPING LIQUORS

FIELD OF THE INVENTION

The present invention relates to the production of organic aldehydes from waste pulping liquor. It is concerned, more particularly, with a process for making syringealdehyde and/or vanillin by alkaline oxidative treatment of waste liquor from alkaline and neutral sulfite pulping operations.

DESCRIPTION OF THE PRIOR ART

There is no commercial production of syringealdehyde, as far as we know. There are known methods of preparing syringealdehyde by synthetic routes, e.g. through several intermediate reactions starting from pyrogallol as disclosed in U.S. Pat. No. 2,516,412, or from vanillin by selective methylation of the 5-hydroxyvanillin derivative (J. Am. Chem. Soc. 74, 4262, 1952). These methods however do not lend themselves to commercial use, and only minute quantities of syringealdehyde have been available in the trade. The potential demand for syringealdehyde, however, has greatly increased, primarily in connection with its usefulness for the production of 3,4,5-trimethoxybenzaldehyde, itself an important drug intermediate.

It is known to produce vanillin from lignin residues obtained from the digestion of wood to cellulosic pulps and a number of commercial processes of this type for the production of vanillin have been in existence for many years. All these processes, however, are based on the processing of lignin from spent sulfite liquor in which the lignin residue is in the form of lignosulfonate. To the best of our knowledge, vanillin has never been produced on a commercial scale from alkaline waste pulping liquors, such as Kraft black liquor.

Vanillin produced by the above processes using an oxidative breakdown of lignin in spent sulfite liquors is often accompanied by syringealdehyde. The quantities of syringealdehyde thus appearing as an impurity vary from very small in the case of lignin originating from coniferous woods to substantial in the case of lignin from pulping deciduous woods.

BRIEF DESCRIPTION OF THE INVENTION

The present invention provides a process for the production of syringealdehyde and/or vanillin from a lignin-containing waste liquor of a hardwood alkaline or neutral sulfite pulping operation in which said lignin-containing waste liquor is mixed with alkali, and, optionally, a catalyst to form a charge, said charge is oxidized under elevated temperature and pressure, the oxidized liquor is extracted with an organic solvent thereby to separate an organic solvent-soluble fraction containing lignin-derived aldehydes from an aqueous fraction containing residual lignin and inorganic compounds, the aqueous fraction is returned to the waste liquor recovery system to recover heat and inorganic compounds, the organic solvent-soluble fraction is treated to extract therefrom a mixture of organic aldehydes, and the mixture of aldehydes is treated to separate syringealdehyde from vanillin.

The single FIGURE of the drawing is a schematic representation of the sequence of steps in the present process including the several cycles of recovery and reuse of the chemicals used at various stages.

DESCRIPTION OF THE PREFERRED EMBODIMENTS

The starting material in the process of the invention is a waste liquor from an alkaline or neutral hardwood pulping operation, e.g. a Kraft block liquor, or a residual liquor from a soda cook or from a neutral sulfite semi-chemical code. Spent liquors from sulfite pulping operations are also suitable, however such liquors have now become less widely available because of the relative decline of the sulfite process. While in the present description reference is made particularly to conventional Kraft liquor, it will be understood that the process may also be used with waste liquors from modified Kraft processes, such as vapour phase Kraft, polysulfide, etc., as well as with other waste liquor as hereinabove stated.

In the normal operation of a Kraft mill, the black liquor collected after separation and washing of the pulp is concentrated by evaporation, e.g. in a multiple effect evaporator, and the concentrated liquor is burnt in a recovery furnace. The combustion of the organic constituents of the liquor provides valuable quantities of heat, e.g. for steam production, while the inorganic constituents collect in the form of a smelt which is recovered and processed back to a composition identical with that of the initial pulping liquor. In accordance with the invention, at least a portion of the black liquor is transferred to a reactor in the aldehyde plant. The liquor to be processed may be withdrawn from the stream of black liquor on the way to recovery, or, in a particular embodiment of the invention, a portion of the cooking liquor may be withdrawn from the digester before the end of the cook.

We have found that there is an advantage in the latter procedure, since with exposure to elevated temperature for an extended time the lignin in the liquor becomes less susceptible to conversion to the desired aldehydes. Naturally, if the latter procedure is used, only a certain percentage of the liquor can be withdrawn from the digester without affecting the yield or quality of the pulp, but it has been found that up to a third of the liquor can be withdrawn from the digester without ill effects. The best time for such withdrawal may have to be determined for particular cook schedules, keeping in mind that in the early stages of the cook the lignin will be highly reactive and convertible to the desired aldehydes at a high yield, but the quantity of lignin dissolved out of the wood will be relatively small, while with the passage of time the quantity of lignin dissolved out will increase but some of the lignin will have undergone thermolytic changes which make it less susceptible to conversion. Since the two tendencies will exist simultaneously, the optimum for any particular cook schedule, species, etc., will best be found experimentally with the help of a few simple measurements on samples of the liquor during the cook.

For the purpose of this process it is preferred to use the black liquor in a partly concentrated condition, e.g. at a concentration of about 25-35% solids. Alkali, such as caustic soda, is added to this liquor in the reactor, so that the ratio of alkali to lignin present in the liquor to be treated is about 0.5 - 3 parts alkali to 1 part lignin on a weight basis. The oxidation is carried out in a known manner by passing air through the alkaline solution at a temperature above 100° C, preferably 140° - 180° C, under pressure of about 50 to 150 psig. A catalyst may be used to increase the yield of aldehyde, such catalyst consisting essentially of a salt of a transition metal capable of readily existing in more than one oxidation stage. Examples of such catalyst are salts of copper, manganese, nickel, iron and cobalt. The oxidation is continued until the yield of syringealdehyde and vanillin has reached a maximum which is generally indicated by a drop in the pH of the solution or a drop in its temperature (in the absence of external) heating), or can otherwise be determined in a simple test for aldehyde content.

As illustrated in the drawing, the oxidized alkaline liquor is neutralized. This can be done, e.g., by carbonation in a suitable vessel, the carbonation being preferably carried out in two stages: in a first stage the oxidized liquor is contacted with scrubbed flue gas, e.g. in a packed tower, until the pH of the liquor is reduced to 9-9.5; and in a second stage the partially carbonated liquor is subjected to pressure carbonation, e.g. with $CO_2$ recovered in the process, under pressure, until the pH of the solution is brought down as close to 7 as possible. Obviously the neutralization can be carried out by treatment with other acids as well, e.g. sulfuric acid. The neutralized solution is then subjected to an extraction with an organic solvent, e.g. benzene, toluene or the like, preferably at a temperature up to 80° C under pressure. The residual aqueous liquor remaining after extraction and containing residual lignin and substantial amounts of caustic is stripped of residues of the organic solvent and of residual $CO_2$, and returned to the pulp mill system for recovery of alkali values. The residual liquor may be added to the concentrated black liquor going to the furnace, or to the "green liquor" in advance of the causticizing stage, depending on circumstances existing in the mill. For example, where the recovery furnace is already operating at capacity, it may be preferable to add the residual liquor to the green liquor, but in normal circumstances it will be more advantageous to add it to the concentrated black liquor on the way to the furnace.

The organic extract containing the desired aldehyde product is concentrated, the recovered solvent being returned for use in the extraction step, and the concentrated solution is treated with an aqueous solution of sodium bisulfite to form a water-soluble sodium bisulfite complex of syringealdehyde and vanillin. The complex is extracted and removed in the aqueous phase, while the organic phase consisting primarily of the solvent (benzene or toluene, or the like) is recovered, purified and returned for re-use in the solvent extraction step. The aqueous extract is washed, e.g. with an alcohol, partially soluble in water, preferably an aliphatic alcohol having a chain of 4– 6 carbons, to remove impurities, and then acidified with sulfuric acid to break up the complex and recover the mixture of aldehydes. The aldehyde mixture separates as a heavy oil which is washed, e.g. with water, to remove excess sulfuric acid, and the washed oil is transferred to further treatment or allowed to cool for storage. The wash water, together with the aqueous phase from the acidification step (from which the $SO_2$ has been removed by heating), may be recycled, e.g. to the initial oxidized liquor, so as to minimize losses of the valuable aldehydes.

The crude aldehyde mixture is treated to separate the syringealdehyde from vanillin. It was found that such separation can be carried out successfully, contrary to established belief in the art, by fractional distillation, provided the mixture is substantially free of acid or alkaline impurities. Hence the importance of the washing steps hereinbefore described. Syringealdehyde of a purity of 99.5% and vanillin of a purity of 99.9% were obtained from the distillation. The products can be further purified by crystalization or other methods.

The process will be further described by means of the following examples which are provided to illustrate, but by no means to limit, the invention.

EXAMPLE 1

In a hardwood Kraft mill cook a portion of the liquor was withdrawn after 1.25 hours of pulping and evaporated to 27.7% W/V (weight per volume) total solids, of which 8.48% was lignin and 2.30% free alkali. An oxidation charge was prepared consisting of 811 cu. ft. of this liquor, 80 cu. ft. of 50% W/W (weight per weight) sodium hydroxide, 20 – 25 lbs ammoniated manganese sulfate and 10 lbs of a defoamer, giving a mixture containing 7.72% W/V of lignin and a ratio of total free alkali to lignin 1.16:1. The mixture was oxidized by passing air through it at a temperature of 140° C, at a pressure of 70 psig, the air flow being about 15,000 cu. ft. per hour.

Samples were taken at regular intervals and analyzed for syringealdehyde and vanillin (S-V) by gas-liquid chromatography. The peak concentration of S+V was 0.439% W/V, reached in 6.5 hours and representing a yield on lignin of 5.69%. The S/V ratio was 2.04:1.

Liquor thus oxidized was treated to produce a crude product, consisting of a mixture of syringealdehyde and vanillin, by the following steps: the oxidized liquor was neutralized by carbonation in two stages, the neutralized liquor was extracted by means of benzene, the organic extract was concentrated and treated with an aqueous solution of sodium bisulfite to form a water-soluble aldehyde-busulfite complex, the aqueous solution of the complex was separated from the organic phase and washed with amyl alcohol, and then treated with sulphuric acid. A heavy oil, consisting of a mixture of syringealdehyde and vanillin, was obtained. The oil was carefully washed with water and removed to storage.

Several samples of the crude product, of about 2 kg each, were subjected to fractional distillation in laboratory apparatus under a vacuum of 120 – 175 microns. Eight consecutive cuts were taken and analyzed by gas-liquid chromatography. In the temperature range 128°– 130° C, (taken on the vapour) after a first cut of vanillin of a purity of 98.5% and amounting to 3.5% of the charge, vanillin of a purity 99.9% was collected totalling 35.1% of the crude mixture. In the temperature range 170°– 172° C syringealdehyde was collected of a purity from 98.8% to 99.8%, totalling 36.1% of the mixture.

An intermediate fraction containing a mixture of vanillin and syringealdehyde and amounting to 12.4% of the charge was collected and recycled to the crude mixture for subsequent distillation. The fraction contained between 84.3% and 87.7% syringealdehyde and the remainder vanillin.

EXAMPLE 2

Waste liquor from a conventional hardwood Kraft cook was evaporated to a total solids (TS) content of 53.7% weight per volume (W/V) which included a lignin content of 11.8% W/V. The black liquor, water and 50% (W/W) sodium hydroxide were mixed in proportions such that the mixture contained 5% W/V of lignin and a ratio of added alkali to lignin of 2:1. A quantity of 1500 ml of this mixture, to which were added 3.65 grams of the catalyst cupric sulfate pentahydrate, was placed in a one-gallon autoclave provided with suitable fittings for the addition and removal of samples and for the addition of air, and also fitted with heaters and a Cavitator stirrer operating at 1400 RPM. The mixture was oxidized by passing air through continuously at the rate of 7 liters per minutes, at a temperature of 165° C (which was reached in ½ hour) and at a pressure of 100 psig. Samples were removed every 15 minutes and analyzed for syringealdehyde and vanillin (S+V) by gas-liquid chromatography. Peak concentration of S+V in the oxidized liquor was reached after 1.5 hours. This concentration was 0.396% W/V of S + V, representing a yield of S + V on lignin of 7.9%. The syringealdehyde to vanillin ratio (S/V) was 2.19:1.

EXAMPLES 3 – 6

Kraft waste liquor from a hardwood cook was processed substantially as in Example 2, except that some of the conditions such as temperature, pressure, lignin concentration, alkali ratio, etc. in the reactor were changed from run to run. Also in some runs ammoniated manganese sulfate in an amount of 0.6g was used as catalyst. These conditions and the resulting yields of syringealdehyde and vanillin are set out below:

pric sulfate catalyst. The temperature of oxidation was 165° C, the pressure 100 psig and the air flow was 7.0 liters per minute. The peak concentration of S+V, reached in 2.5 hours, was 0.597% W/V, representing a yield on lignin of 11.94%. The S/V ratio was 2.43:1.

EXAMPLES 8 – 11

Early stage Kraft waste liquors, similar to the one used in Example 7, were used for the preparation of syringealdehyde and vanillin substantially as described in preceding examples with variations in the initial composition of the liquor and in the conditions of the oxidation. The liquors used were removed from the digester 1.25 – 1.5 hours after the start of pulping and were of the following composition:

| Example | Run No. | Total solids % W/V | Lignin % W/V | Alkali % W/V |
|---|---|---|---|---|
| 8 | 261 | 24.0% | 5.67% | 1.09% |
| 9 | 310 | 26.9% | 5.48% | 3.04% |
| 10 | 284 | 23.2% | 4.17% | |
| 11 | 286 | 23.2% | 4.17% | 2.28% |

The oxidation charge was, as before, 1500 ml and the

| Example | Run No. | Temp. (° C) | Pressure (psig) | Air flow (l/m) | Lignin Concentr. (W/V%) | Alkali To lignin ratio | Catalyst | S+V (W/V%) | S+V Yield on lignin % | S/V ratio |
|---|---|---|---|---|---|---|---|---|---|---|
| 3 | 338 | 165° C | 100 | 7 l/m | 7.65% | 1.36:1 | Cu SO₄ | .454% | 5.96% | 1.97:1 |
| 4 | 329 | 141° C | 70 | 0.4 l/m | " | " | Mn SO₄ | .411% | 5.39% | 1.92:1 |
| 5 | 345 | " | " | " | 8.08% | 1.3:1 | " | .371% | 4.64% | 2.25:1 |
| 6 | 348 | " | " | " | 8.65% | 1.4:1 | " | .373% | 4.31% | 2.05:1 |

EXAMPLE 7

This example illustrates further the use of early stage Kraft waste liquor, i.e. liquor removed from the digester before the completion of the cook. Such liquor was found to contain lignin in a form more amenable to conversion to S+V, but the lignin is in lower concentration than in a liquor withdrawn after completion of the cook. A sample of lignin was taken from the digester one hour after the start of steaming. It contained 22.7% total solids, of which 3.2% lignin, and 1.69% free alkali as sodium hydroxide (all W/V). The liquor was evaporated in the laboratory to 6%W/V lignin and after mixing with alkali and water the oxidation charge of 1500 ml contained 5% W/V of lignin, a ratio of total alkali to lignin of 2.53:1, and a quantity of 3.65g of cucatalyst was either cupric sulfate pentahydrate in the amount of 3.65g or ammoniated manganese sulfate in the amount of 0.6g. The conditions in the reactor were:

| Example | Temp. | Pressure (psig) | Air flow (l/m) | Lignin Concentr. (W/V%) | Alkali to lignin ratio | Catalyst | S+V (W/V%) | S+V yield on lignin (%) | S/V ratio |
|---|---|---|---|---|---|---|---|---|---|
| 8 | 165° C | 100 | 7 | 5% | 2.19:1 | Cu SO₄ | 0.454% | 8.68% | 1.63:1 |
| 9 | " | " | " | " | 2.0:1 | " | 0.466% | 9.32% | 1.59:1 |
| 10 | 141° C | 70 | 0.4 | " | 2.0:1 | Mn SO₄ | 0.492% | 13.08% | 1.94:1 |
| 11 | 125° C | 70 | 0.4 | " | 2.0:1 | " | 0.435% | 11.39% | 1.96:1 |

EXAMPLES 12 – 14

A hardwood NSSC waste liquor collected from the pressafiner of an NSSC operation had a total solids content of 20.5% W/V and a lignin content of 2.81%. The liquor was evaporated in the laboratory prior to oxidation. The 1500 ml oxidation. The 1500 ml oxidation charge was processed substantially as hereinabove described the conditions in the reactor being as follows:

| Example | Temp. (° C) | Pressure (psig) | Air flow (l/min) | Lignin Concent. (% W/V) | Alkali to lignin | Catalyst | S+V (W/V%) | S+V yield on lignin (W/V%) | S/V ratio |
|---|---|---|---|---|---|---|---|---|---|
| 12 | 165° C | 100 | 1.5 l/m | 5% | 1.6:1 | Cu SO₄ | .933% | 18.67% | 1.52 |
| 13 | 150° C | 85 | 1.2 l/m | 8.45% | .85:1 | " | .763% | 9.04 | 1.67 |
| 14 | 143° C | 70 | .4 l/m | 4.57% | 1.75:1 | Mu SO₄ | .429% | 9.40% | 1.66 |

The invention permits the production of valuable chemical compounds, notably syringealdehyde and vanillin from kraft and similar waste liquor, thus providing a new practically limitless source for these chemicals, the demand for which is now growing and the use of which as chemical intermediates becomes ever greater.

What we claim is:

1. The process for the production of syringealdehyde from a lignin-containing waste liquor of a hardwood kraft pulping operation comprising: forming a charge of said waste liquor and alkali, passing oxygen-containing gas in intimate contact with said charge in a reactor under elevated temperature and pressure thereby to oxidize said liquor, neutralizing said oxidized liquor, extracting said neutralized oxidized liquor with an organic solvent thereby to separate an organic fraction soluble in said organic solvent from an aqueous fraction containing residual lignin and inorganic chemicals, recycling said aqueous fraction to the kraft pulping operation to recover alkali values from said fraction, treating said organic fraction with an aqueous solution of sodium bisulfite to form from part of said organic fraction an aqueous solution of a sodium bisulfite complex of syringealdehyde and vanillin, separating said aqueous solution of said complex from the remainder of said organic fraction, washing said aqueous solution of said complex with an aliphatic alcohol having a chain of 4–6 carbons, acidifying said washed aqueous solution to break up said complex and form an oil consisting essentially of a mixture of syringealdehyde and vanillin, and separating syringealdehyde from vanillin by fractional distillation.

2. The process of claim 1 wherein said lignin-containing waste liquor is a liquor withdrawn from a kraft digester before the termination of the cook.

3. The process of claim 1 wherein the charge contains about 0.5 –3 parts of alkali to 1 part of lignin - contained in said waste liquor.

4. The process of claim 1 wherein the charge contains a catalyst consisting of one of the group consisting of salts of copper, manganese, nickel, iron and cobalt.

5. The process of claim 1 wherein the oxygen-containing gas is passed in contact with said charge under a temperature above 100° C under pressure between 50 and 150 psig.

6. The process of claim 1 wherein said aliphatic alcohol having a chain of 4–6 carbons is amyl alcohol.

* * * * *